United States Patent
Waki

(10) Patent No.: US 8,004,291 B2
(45) Date of Patent: Aug. 23, 2011

(54) BIOELECTRIC IMPEDANCE MEASURING CIRCUIT

(75) Inventor: Naosumi Waki, Kanagawa (JP)

(73) Assignee: Mitsumi Electric Co., Ltd., Tokyo (JP)

( * ) Notice: Subject to any disclaimer, the term of this patent is extended or adjusted under 35 U.S.C. 154(b) by 294 days.

(21) Appl. No.: 11/831,000

(22) Filed: Jul. 31, 2007

(65) Prior Publication Data

US 2008/0036475 A1 Feb. 14, 2008

(30) Foreign Application Priority Data

Aug. 8, 2006 (JP) .................................. 2006-216130

(51) Int. Cl.
*G01R 27/08* (2006.01)

(52) U.S. Cl. ........................................ 324/692; 324/691

(58) Field of Classification Search .................... 324/692
See application file for complete search history.

(56) References Cited

U.S. PATENT DOCUMENTS

| | | | |
|---|---|---|---|
| 3,871,359 A | | 3/1975 | Pacela |
| 5,086,781 A * | | 2/1992 | Bookspan ..................... 600/547 |
| 6,208,890 B1 * | | 3/2001 | Sarrazin et al. ............... 600/547 |
| 6,292,690 B1 * | | 9/2001 | Petrucelli et al. ............ 600/547 |
| 6,472,888 B2 * | | 10/2002 | Oguma et al. ................ 324/691 |
| 6,473,641 B1 * | | 10/2002 | Kodama et al. ............... 600/547 |
| 6,473,643 B2 * | | 10/2002 | Chai et al. ..................... 600/547 |
| 6,631,292 B1 | | 10/2003 | Liedtke |
| 7,233,823 B2 * | | 6/2007 | Simond et al. ................ 600/547 |
| 2002/0062090 A1 | | 5/2002 | Chai et al. |
| 2004/0127811 A1 | | 7/2004 | Higuchi |
| 2006/0004300 A1 * | | 1/2006 | Kennedy ........................ 600/547 |

FOREIGN PATENT DOCUMENTS

| | | |
|---|---|---|
| EP | 1121898 | 8/2001 |
| JP | 2001-161655 | 6/2001 |
| WO | WO03/077753 | 9/2003 |

OTHER PUBLICATIONS

JP 2001-161655, Masato, Machine translation.*
Green, D. C., Digital Electronics, $5^{th}$ edition, Addison Wesley Longman, England, 1986, p. 328-342.*

* cited by examiner

*Primary Examiner* — Thomas Valone
(74) *Attorney, Agent, or Firm* — Ladas & Parry LLP

(57) ABSTRACT

A bioelectric impedance measuring circuit for applying a current to an organism and measuring a bioelectric impedance of the organism is disclosed that includes a pseudo-sine wave generating circuit for generating a pseudo-sine wave based on an input square wave, a voltage/current converting circuit for outputting current to the organism in correspondence with the pseudo-sine wave generated by the pseudo-sine wave generating circuit, and a processing circuit for generating the square wave and supplying the square wave to the pseudo-sine wave generating circuit and measuring the bioelectric impedance based on a voltage output from the voltage/current converting circuit. The pseudo-sine wave generating circuit is included in a semiconductor integrated circuit.

8 Claims, 5 Drawing Sheets

BIOELECTRIC IMPEDANCE MEASURING CIRCUIT

BACKGROUND OF THE INVENTION

1. Field of the Invention

The present invention generally relates to a bioelectric impedance measuring apparatus, and more particularly to a bioelectric impedance measuring circuit for supplying electric current to and measuring bioelectric impedance of an organism.

2. Description of the Related Art

There is known a body fat measuring system that measures the percentage of body fat of an organism by measuring the bioelectric impedance of the organism (see, for example, Japanese Laid-Open Patent Application No. 2001-161655).

FIG. 5 is a block diagram showing a configuration of a body fat measuring system 10 according to a related art case.

The body fat measuring system 10 includes a CPU 11, a passive filter 12, a voltage/current converting circuit 13, electrodes 14, 15, a voltage detecting circuit 16, an input apparatus 17, and a display apparatus 18.

The CPU 11 is for outputting a square wave(s) according to a measurement start instruction (instruction to start measurement) from the input apparatus 17. The square wave output by the CPU 11 is supplied to the passive filter 12. The passive filter 12 shapes (waveform shaping) the supplied square wave into a sine wave (sinusoidal wave). The waveform-shaped sine wave is supplied to the voltage/current converting circuit 13.

The voltage/current converting circuit 13 converts (transforms) the sine wave received from the passive filter 12 into electric current and supplies the converted electric current to an organism from the electrode 14. The current supplied by the electrode 14 flows to ground via the electrode 15.

The voltage detecting circuit 16 detects the voltage of the electrode 14 and supplies the voltage to the CPU 11. The CPU 11 measures the bioelectric impedance of the organism based on the amplitude of the voltage supplied from the voltage detecting circuit 16, to thereby obtain, for example, the percentage of fat of the organism. The measurement result of the CPU 11 is supplied to the display apparatus 18 and displayed by the display apparatus 18.

Thus, in a bioelectric impedance measuring circuit according to a related art case, a passive filter is used for converting a square wave from a CPU into a sine wave. Since the passive filter requires a relatively large inductor and a capacitor, it cannot be included (mounted) in a semiconductor integrated circuit.

SUMMARY OF THE INVENTION

The present invention may provide a bioelectric impedance measuring circuit that substantially obviates one or more of the problems caused by the limitations and disadvantages of the related art.

Features and advantages of the present invention will be set forth in the description which follows, and in part will become apparent from the description and the accompanying drawings, or may be learned by practice of the invention according to the teachings provided in the description. Objects as well as other features and advantages of the present invention will be realized and attained by a bioelectric impedance measuring circuit particularly pointed out in the specification in such full, clear, concise, and exact terms as to enable a person having ordinary skill in the art to practice the invention.

To achieve these and other advantages and in accordance with the purpose of the invention, as embodied and broadly described herein, an embodiment of the present invention provides a bioelectric impedance measuring circuit for applying a current to an organism and measuring a bioelectric impedance of the organism, the bioelectric impedance measuring circuit including: a pseudo-sine wave generating circuit for generating a pseudo-sine wave based on an input square wave; a voltage/current converting circuit for outputting current to the organism in correspondence with the pseudo-sine wave generated by the pseudo-sine wave generating circuit; and a processing circuit for generating the square wave and supplying the square wave to the pseudo-sine wave generating circuit and measuring the bioelectric impedance based on a voltage output from the voltage/current converting circuit; wherein the pseudo-sine wave generating circuit is included in a semiconductor integrated circuit.

In the bioelectric impedance measuring circuit according to an embodiment of the present invention, the pseudo-sine wave generating circuit may include a filter for smoothing the pseudo-sine wave and supplying the pseudo-sine wave to the voltage/current converting circuit.

In the bioelectric impedance measuring circuit according to an embodiment of the present invention, the processing circuit, the pseudo-sine wave generating circuit, and the voltage/current converting circuit may be included in a semiconductor integrated circuit of a single chip.

In the bioelectric impedance measuring circuit according to an embodiment of the present invention, the pseudo-sine wave generating circuit and the voltage/current converting circuit may be included in a semiconductor integrated circuit of a single chip.

In the bioelectric impedance measuring circuit according to an embodiment of the present invention, the pseudo-sine wave generating circuit may include plural resistors for dividing voltage from a power source, plural switching devices for outputting a voltage divided by the plural resistors, and a controller for sequentially switching on the plural switching devices based on the square wave.

Other objects and further features of the present invention will be apparent from the following detailed description when read in conjunction with the accompanying drawings.

DESCRIPTION OF THE PREFERRED EMBODIMENTS

In the following, embodiments of the present invention are described with reference to the accompanying drawings.

Figure 1:
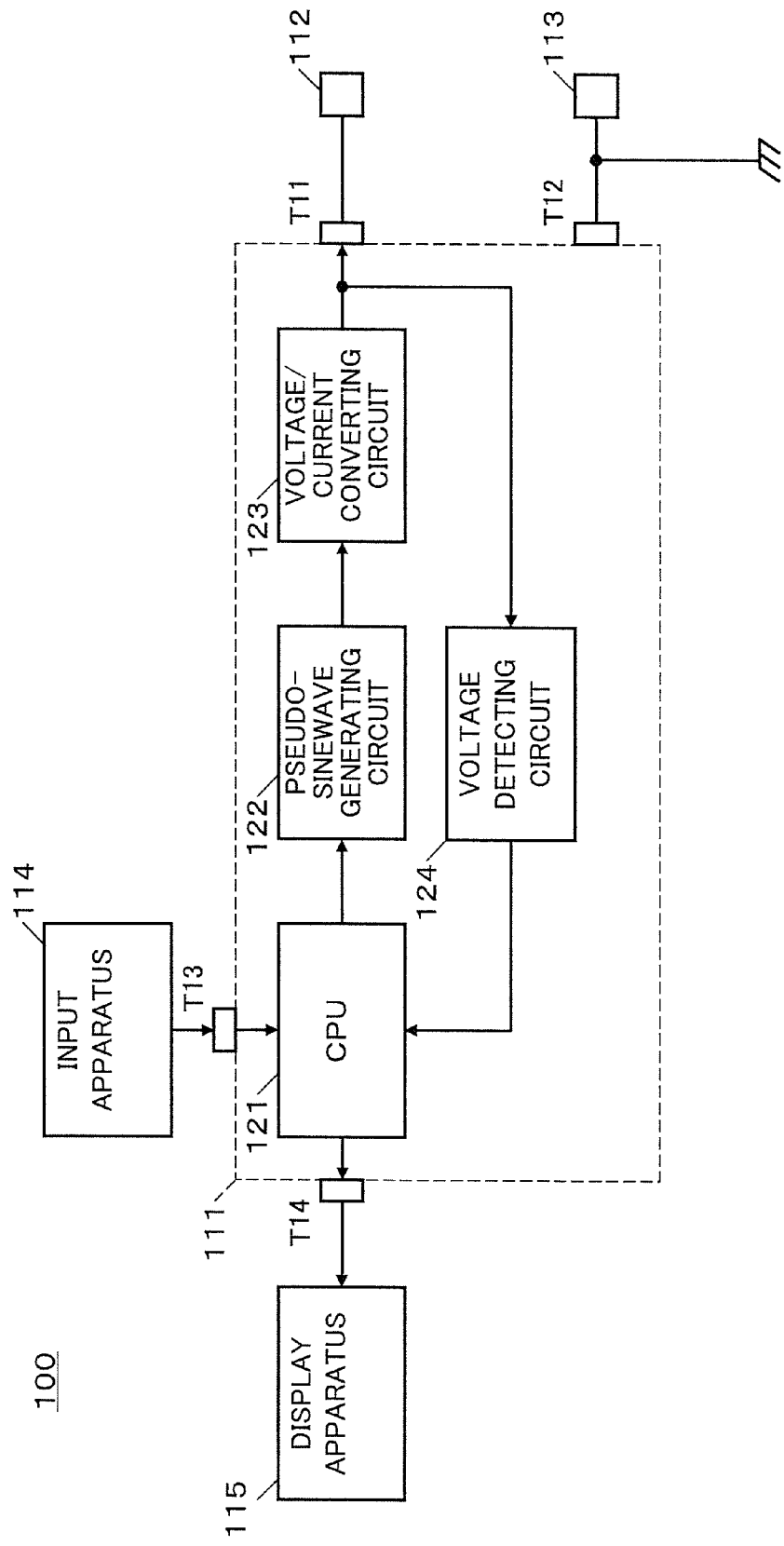
FIG. 1 is a block diagram showing a body-fat measuring system according to a first embodiment of the present invention.

FIG. 1 is a block diagram showing a body-fat measuring system 100 according to a first embodiment of the present invention.

The body-fat measuring system 100 includes a bioelectric impedance measuring circuit 111, electrodes 112, 113, an input apparatus 114, and a display apparatus 115.

The bioelectric impedance measuring circuit 111 is configured as a semiconductor integrated circuit of a single chip. The bioelectric impedance measuring circuit 111 includes a CPU (processing circuit) 121, a pseudo-sine wave generating circuit 122, a voltage/current converting circuit 123, and a voltage detecting circuit 124.

The CPU 121 is for generating a clock based on a measurement start instruction from the input apparatus 114 and supplying the generated clock to the pseudo-sine wave generating circuit 122.

The pseudo-sine wave generating circuit 122 is for generating a pseudo-sine wave(s) based on the clock from the CPU 121.

Figure 2:
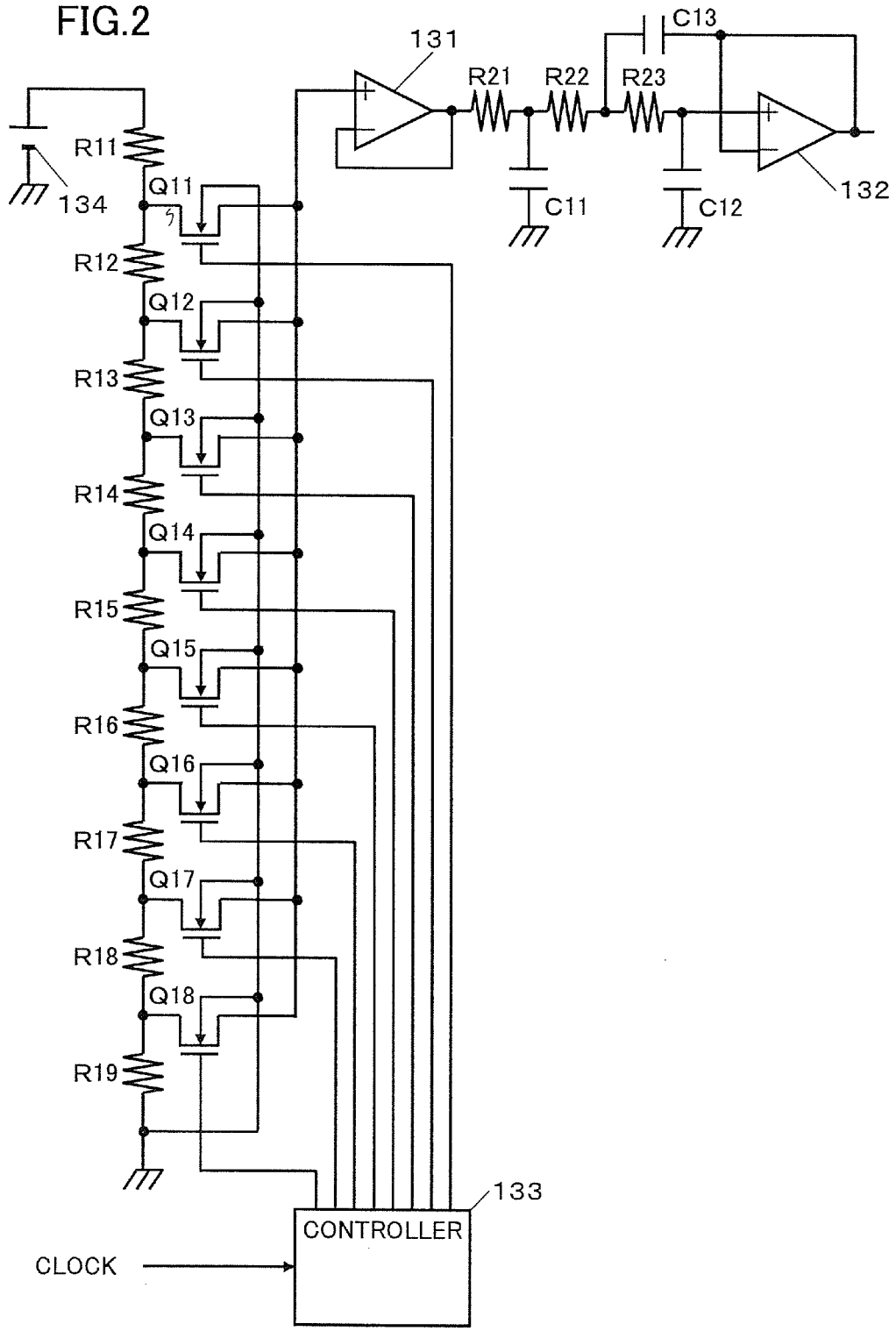
FIG. 2 is a circuit diagram of a pseudo-sine wave generating circuit according to an embodiment of the present invention.

FIG. 2 is a circuit diagram of the pseudo-sine wave generating circuit 122 according to an embodiment of the present invention.

The pseudo-sine wave generating circuit 122 includes differential amplifiers 131, 132, a controller 133, a power source 134, resistors R11-R19, R21-R23, transistors (switching devices) Q11-Q18, and condensers C11-C13.

The resistors R11-R19, which are connected in series between the power source 134 and ground, divide the voltage (power source voltage) applied from the power source 134. The transistor Q11 has its source connected to a connection point between the resistors R11 and R12. The transistor Q12 has its source connected to a connection point between the resistors R12 and R13. The transistor Q13 has its source connected to a connection point between the resistors R13 and R14. The transistor Q14 has its source connected to the resistors R14 and R15. The transistor Q15 has its source connected to a connection point between the resistors R15 and R16. The transistor Q16 has its source connected to a connection point between the resistors R16 and R17. The transistor Q17 has its source connected to a connection point between the resistors R17 and R18. The transistor Q18 has its source connected to a connection point between the resistors R18 and R19. Furthermore, the drains of the transistors Q11-Q18 are connected to a non-inverting input terminal of the differential amplifier 131. Moreover, the controller 133 supplies a control signal(s) to each corresponding gate of the transistors Q11-Q18. It is to be noted that the sources and the drains of the transistors Q11-Q18 may be connected in reverse.

The transistors Q11-Q18 are switched according to the control signals from the controller 133, so that the voltages divided by the resistors R11-R19 can be sequentially selected and output.

For example, the transistors Q11-Q18 may be controlled by the control signals from the controller 133 so that the transistors Q11-Q18 are sequentially switched on in an order of transistor Q11→transistor Q12→transistor Q13→transistor Q14→transistor Q15→transistor Q16→transistor Q17→transistor Q18→transistor Q18→transistor Q17→transistor Q16→transistor Q15→transistor Q14→transistor Q13→transistor Q12→transistor Q11. The controller 133 is for repeating the above operation based on the clock(s) from the CPU 121.

Figure 3:
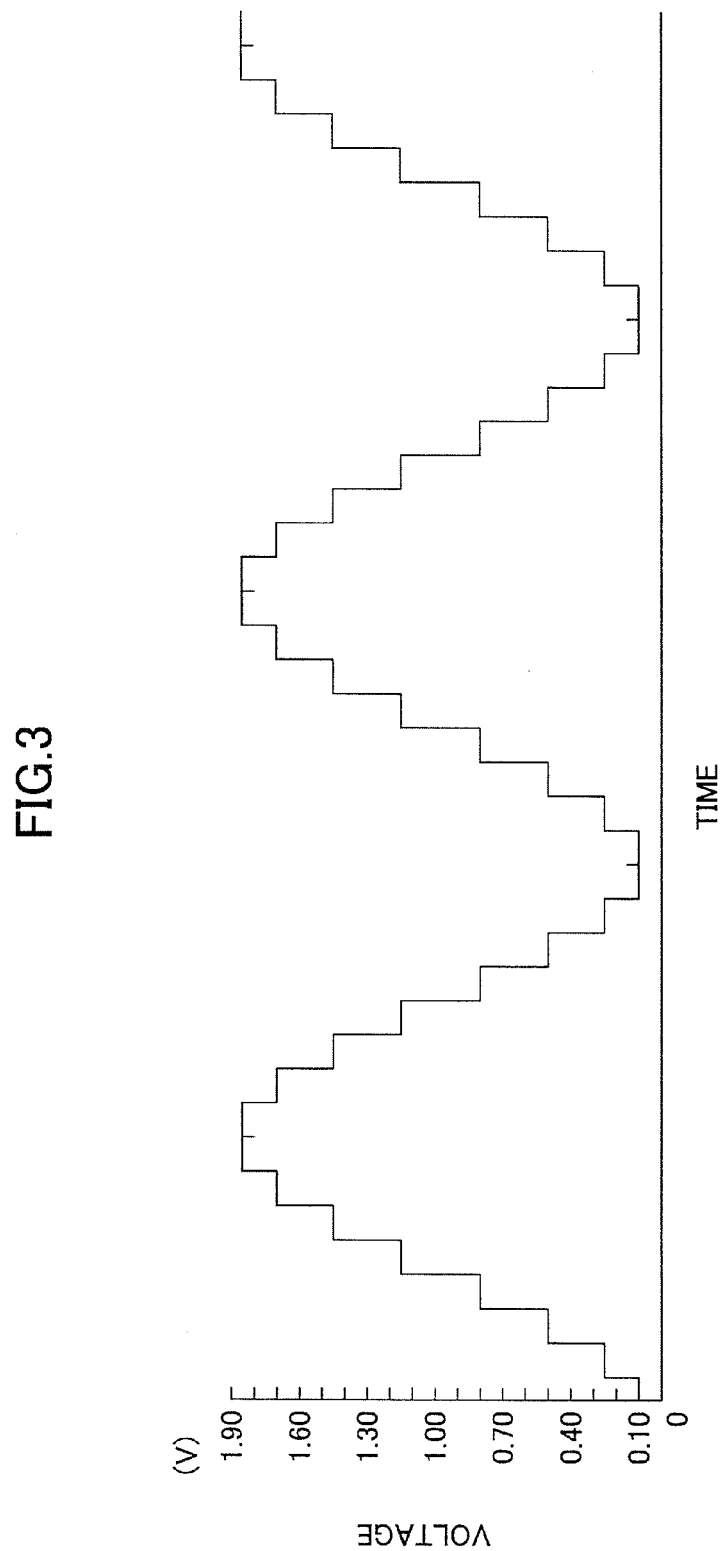
FIG. 3 is a schematic diagram for describing a waveform (output waveform) output by a differential amplifier according to an embodiment of the present invention.

FIG. 3 is a schematic diagram for describing a waveform (output waveform) output by the differential amplifier 131 according to an embodiment of the present invention.

As shown in FIG. 3, the output waveform of the differential amplifier 131 sequentially increases and decreases in a sinusoidal shape in correspondence with the clocks from the CPU 121.

In this case, the resistors R11-R19 are set so that the waveforms corresponding to the sequentially selected voltages are proximate to the waveform of a sine wave (sinusoidal wave). For example, with respect to the waveform of the sine wave shown in FIG. 3, the resistors R11-R19 are set to satisfy a relationship of R11 (=R19)<R12 (=R18)<R13 (=R17)<R14 (=R16)<R15.

The selected output voltage from the transistors Q11-Q18 is supplied to the differential amplifier 131. The differential amplifier 131 is configured as a buffer amplifier.

The output of the differential amplifier is supplied to an active filter. The active filter includes resistors R21-R23, condensers C11-C13, and a differential amplifier 132. The active filter performs smoothing on a pseudo-sine wave signal output from the differential amplifier 131 and supplies the smoothed signal to the voltage/current converting circuit 123.

The voltage/current converting circuit 123 converts the pseudo-sine wave signal supplied from the pseudo-sine wave generating circuit 122 into electric current. The current converted in correspondence with the pseudo-sine wave signal by the voltage/current converting circuit 123 is output from a terminal T11. The terminal T11 is connected to the electrode 112. The electrode 112 is in contact with the organism for supplying current to the organism. It is to be noted that the current supplied from the electrode 112 to the organism is controlled to be, for example, a maximum of approximately 500 μA.

The electrode 113 is also in contact with the organism. The electrode 113 is grounded so that the current supplied from the electrode 12 to the organism can flow to ground.

The voltage detection circuit 124, which is connected to the terminal T11, is for detecting the voltage of the electrode 112. The voltage detected by the voltage detecting circuit 124 is supplied to the CPU 121.

The CPU 121 measures the bioelectric impedance of the organism based on the amplitude of the voltage supplied from the voltage detecting circuit 124 and estimates the percentage of fat of the organism based on the measured bioelectric impedance. The CPU 121 supplies the data of the estimated fat percentage to the display apparatus 115. The display apparatus 115, which includes a display driver, a LCD (Liquid Crystal Display), etc., is for driving the LCD and displaying fat percentage based on the fat percentage data supplied from the CPU 12.

With the above-described exemplary configuration of the pseudo-sine wave generating circuit 122, the pseudo-sine wave generating circuit 122 can generate pseudo-sine waves by dividing voltage of the power source 134 with the resistors R11-R19 and outputting the divided voltages of the resistors R11-R19 by sequentially switching on the transistors Q11-Q19 according to the clocks from the CPU 121. Thereby, unlike a passive filter, the pseudo-sine wave generating circuit according to the above-described embodiment of the present invention requires no inductor or capacitor. Accordingly, the pseudo-sine wave generating circuit 122 can be included in a semiconductor integrated circuit. Thus, the CPU 121, the pseudo-sine wave generating circuit 122, the voltage/current converting circuit 123, and the voltage detecting circuit 124 can be included in a semiconductor integrated circuit on a single chip.

Although a filter including resistors R21-R23, condensers C11-C13, and the differential amplifier 132 is provided for smoothing the pseudo-sine waves output from the differential amplifier 131 according to the above-described embodiment of the present invention, the pseudo-sine waves output from the differential amplifier 132 may be supplied to the voltage/current converting circuit 123.

Figure 4:
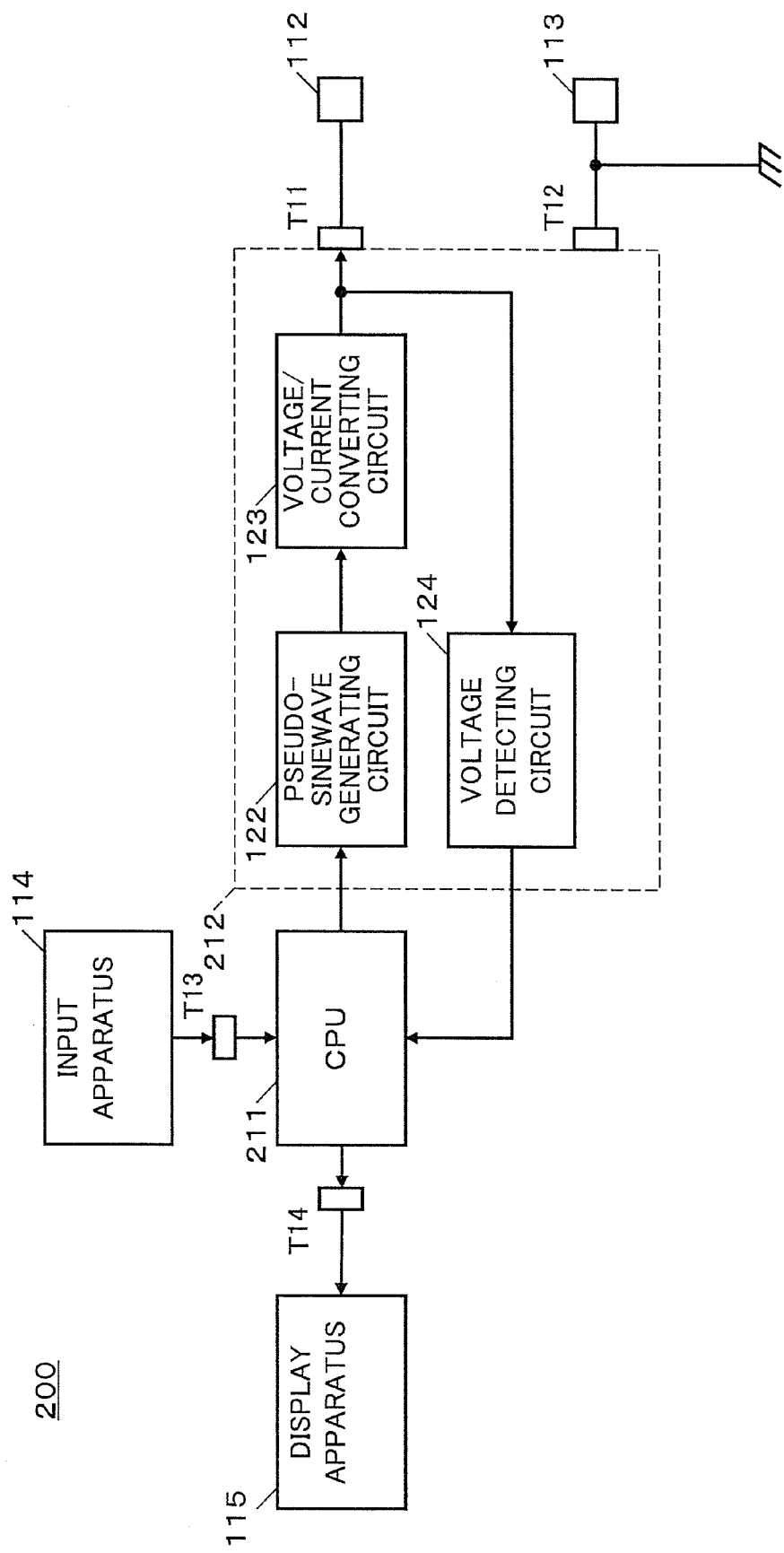
FIG. 4 is a block diagram showing a body-fat measuring system according to a second embodiment of the present invention.
Figure 5:
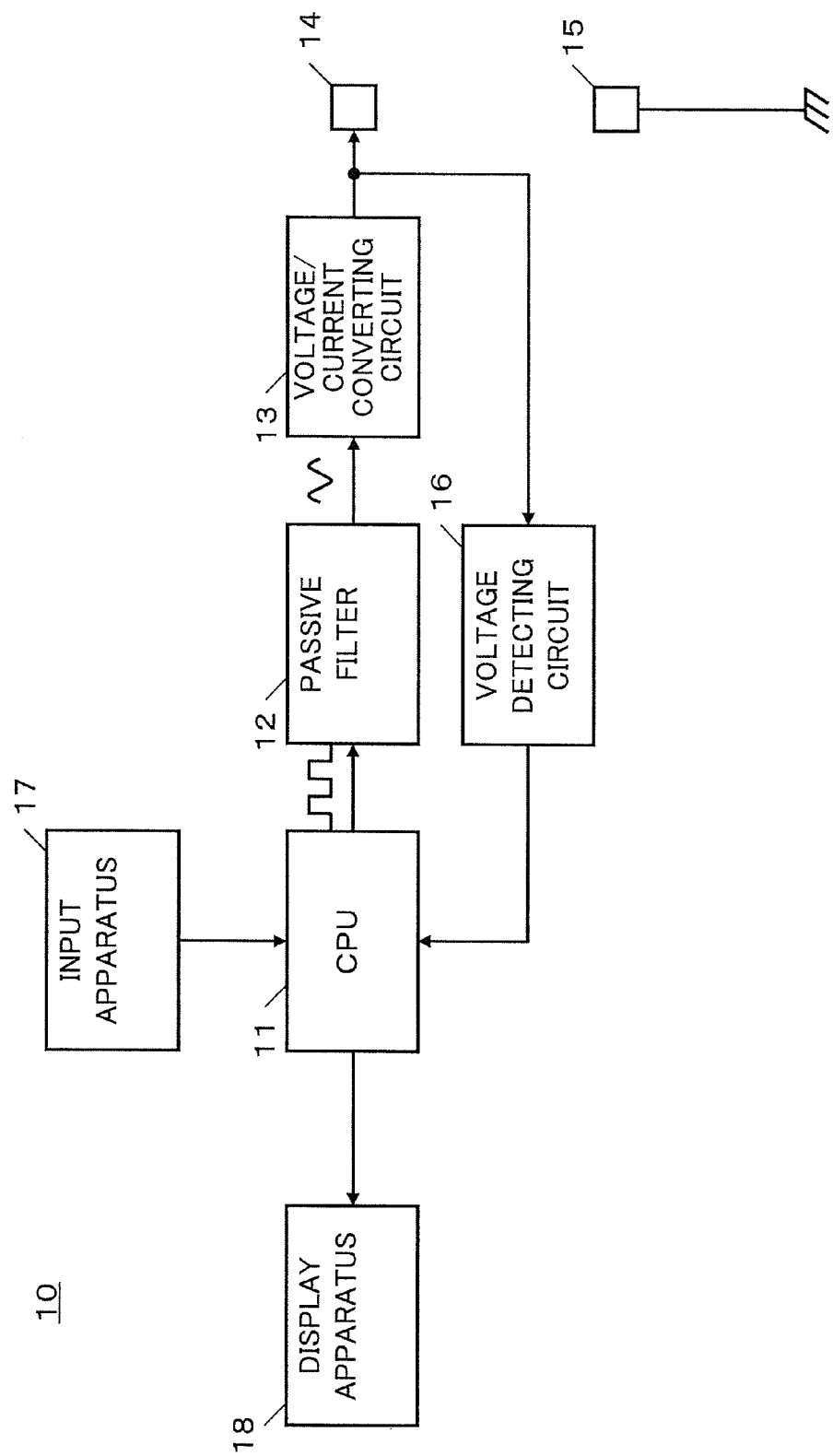
FIG. 5 is a block diagram showing a configuration of a body fat measuring system according to a related art case.

FIG. 4 is a block diagram showing a body-fat measuring system 200 according to a second embodiment of the present invention. In FIG. 4, like components are denoted by like reference numerals as of FIG. 1 and are not further explained.

The body-fat measuring system 200 has a bioelectric impedance measuring circuit 111 including a CPU 211 and a pseudo-sine wave generating IC 212. The CPU 211 and the pseudo-sine wave generating circuit IC 212 are separately included in different semiconductor integrated circuits.

The CPU 211 is for performing the same processes as those of the CPU 121 of the first embodiment of the present invention. The pseudo-sine wave generating IC 212 is configured as a semiconductor integrated circuit of a single chip. The pseudo-sine wave generating IC 212 includes the pseudo-sine wave generating circuit 122, the voltage/current converting circuit 123, and the voltage detecting circuit 124 of the first embodiment of the present invention.

With the above-described body-fat measuring system 200 according to the second embodiment of the present invention, the CPU 211 to be used can be freely selected. For example, the CPU 211 can easily be changed to a high performance CPU 211. This improves the degree of freedom in designing a body-fat measuring system having a bioelectric impedance measuring circuit.

Thus, since a small device as the pseudo-sine wave generating circuit 122 can be included (mounted) in a semiconductor integrated circuit for generating pseudo-sine waves from square waves from the CPU (i.e. processing circuit) 121 or 211, the bioelectric impedance measuring circuit can be fabricated with a small size.

Further, the present invention is not limited to these embodiments, but variations and modifications may be made without departing from the scope of the present invention.

The present application is based on Japanese Priority Application No. 2006-216130 filed on Aug. 8, 2006, with the Japanese Patent Office, the entire contents of which are hereby incorporated by reference.

What is claimed is:

1. A bioelectric impedance measuring circuit for applying a current to an organism and measuring a bioelectric impedance of the organism, the bioelectric impedance measuring circuit comprising:
    a pseudo-sine wave generating circuit for generating a pseudo-sine wave based on an input square wave;
    a voltage/current converting circuit for outputting current to the organism in correspondence with the pseudo-sine wave generated by the pseudo-sine wave generating circuit; and
    a processing circuit for generating the square wave and supplying the square wave to the pseudo-sine wave generating circuit and measuring the bioelectric impedance based on a voltage output from the voltage/current converting circuit;
    wherein the pseudo-sine wave generating circuit is included in a semiconductor integrated circuit;
    wherein the pseudo-sine wave generating circuit includes:
    a plurality of serially connected resistors for dividing voltage from a power source,
    a plurality of switching devices for outputting a voltage divided by the plurality of resistors, each of the plural switching devices has a source connected to a connecting point connecting a pair of the plural resistors, and
    a controller for sequentially switching on the plurality of switching devices based on the square wave.

2. The bioelectric impedance measuring circuit as claimed in claim 1, wherein the processing circuit, the pseudo-sine wave generating circuit, and the voltage/current converting circuit are included in a semiconductor integrated circuit of a single chip.

3. The bioelectric impedance measuring circuit as claimed in claim 1, wherein the pseudo-sine wave generating circuit and the voltage/current converting circuit are included in a semiconductor integrated circuit of a single chip.

4. The bioelectric impedance measuring circuit as claimed in claim 1, wherein the pseudo-sine wave generating circuit includes:
    a plurality of resistors for dividing voltage from a power source;
    a plurality of switching devices for selecting the voltage divided by the plurality of resistors,
    wherein the pseudo-sine wave generating circuit is configured to select the voltage divided by the plurality of resistors by switching on/off the plurality of switching devices.

5. The bioelectric impedance measuring circuit as claimed in claim 1, wherein the controller is configured to sequentially switch on the plural switching devices in order by transmitting a control signal to the plural switching devices based on the square wave.

6. The bioelectric impedance measuring circuit as claimed in claim 1, further comprising:
    a differential amplifier configured to output a pseudo-sine wave signal according to the voltage output from the plural switching devices.

7. The bioelectric impedance measuring circuit as claimed in claim 1, wherein the plurality of resistors are connected in series.

8. The bioelectric impedance measuring circuit as claimed in claim 7, wherein each of the switching devices includes a first terminal connected between any two of the plurality of resistors and a second terminal outputting a divided voltage, such that each switching device, when switched on by the controller, outputs a different divided voltage whereby the pseudo-sine wave is generated when the controller sequentially switches on the plurality of switching devices.

* * * * *